(12) United States Patent
Berndtsson et al.

(10) Patent No.: US 7,833,746 B2
(45) Date of Patent: Nov. 16, 2010

(54) BLOOD TEST INSTRUMENT USING A DISPOSABLE CARTRIDGE

(75) Inventors: Ingemar Berndtsson, Sollentuna (SE); Lars Svensson, Vallentuna (SE); Lennart Niklason, Sollentuna (SE)

(73) Assignee: Boula Medical AB, Stockholm (SE)

( * ) Notice: Subject to any disclaimer, the term of this patent is extended or adjusted under 35 U.S.C. 154(b) by 16 days.

(21) Appl. No.: 12/118,603

(22) Filed: May 9, 2008

(65) Prior Publication Data

US 2008/0220464 A1  Sep. 11, 2008

Related U.S. Application Data

(62) Division of application No. 10/533,790, filed as application No. PCT/SE03/01796 on Nov. 19, 2003, now Pat. No. 7,608,223.

(30) Foreign Application Priority Data

Nov. 20, 2002 (SE) .................................. 0203435

(51) Int. Cl.
*C12Q 1/02* (2006.01)
(52) U.S. Cl. ....................................................... 435/29
(58) Field of Classification Search .................... 435/29
See application file for complete search history.

(56) References Cited

U.S. PATENT DOCUMENTS

| 5,230,866 A | 7/1993 | Shartle et al. |
| 5,652,149 A | 7/1997 | Mileaf et al. |
| 6,284,548 B1 | 9/2001 | Berndtsson |
| 6,387,328 B1 | 5/2002 | Berndtsson |

FOREIGN PATENT DOCUMENTS

| EP | 0306158 A2 | 3/1989 |
| EP | 1 203 959 A1 | 5/2002 |
| WO | WO-93/17328 A1 | 9/1993 |
| WO | WO-99/01742 A1 | 1/1999 |
| WO | WO-01/75416 A1 | 10/2001 |
| WO | WO-02/18785 A1 | 3/2002 |
| WO | WO-03/044488 A1 | 5/2003 |

*Primary Examiner*—Walter D Griffin
*Assistant Examiner*—Bobby Ramdhanie
(74) *Attorney, Agent, or Firm*—Latimer IP Law, LLP

(57) ABSTRACT

A blood test instrument using a disposable cartridge and a method of measuring a blood sample using the instrument are disclosed. The instrument includes a cell counting station for counting blood cells by electrical resistance measurement, a pressure actuating component adapted to apply a pressure alternately on two flexible receptacles of a disposable cartridge removably placed in the instrument to cause flowing of a mixture of a blood sample and a liquid agent between the two receptacles to obtain proper mixing, and a conduit adapted to deliver the mixture to the cell counting station for counting. After measuring the blood sample, the instrument withdraws a washing liquid contained in another receptacle of the disposable cartridge and uses the washing liquid to clean the instrument and to deliver the mixture back to the cartridge for disposal.

15 Claims, 7 Drawing Sheets

Transport position

Sampling

First mixing

Second mixing

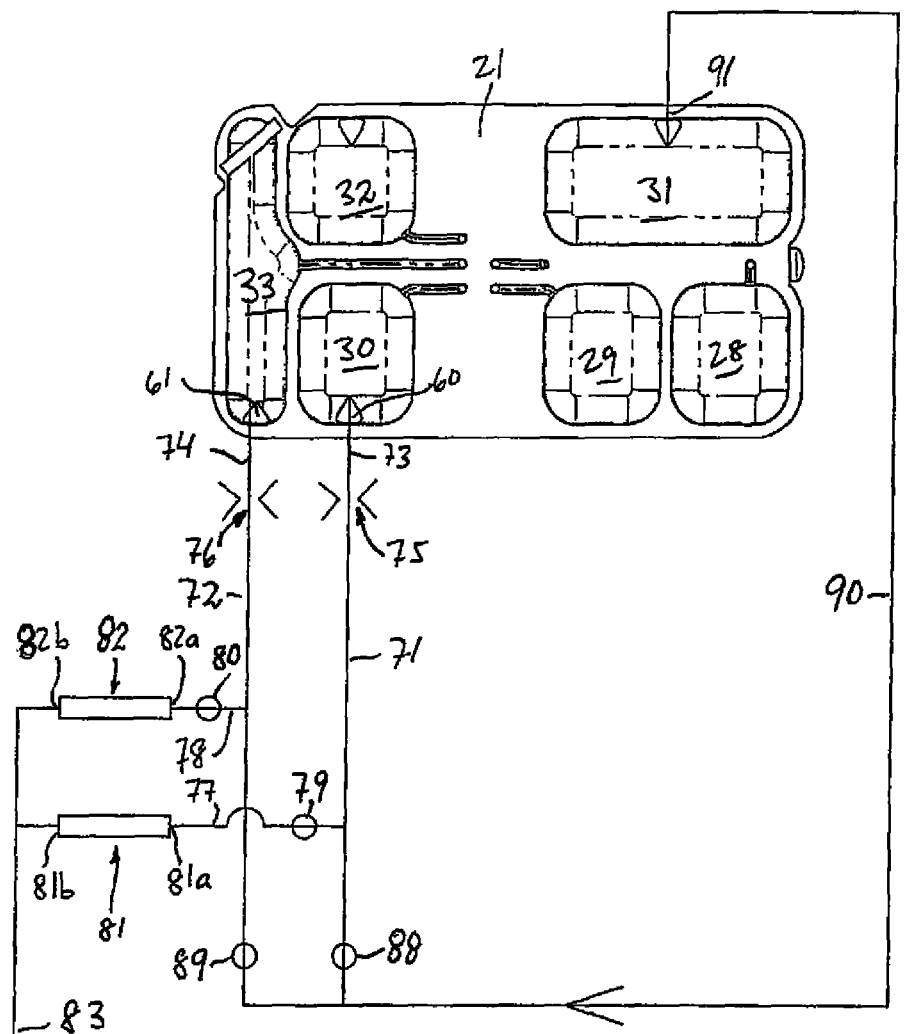
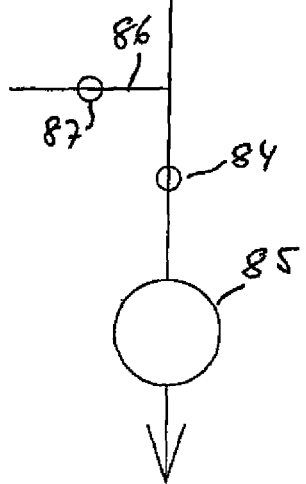
Fig. 11

BLOOD TEST INSTRUMENT USING A DISPOSABLE CARTRIDGE

This application is a divisional of patent application Ser. No. 10/533,790, filed May 4, 2005, which is the national phase application of International Patent Application No. PCT/SE03/01796, filed Nov. 19, 2003, now U.S. Pat. No. 7,608,223, which claims priority of Sweden Patent Application No. 0203435-3, filed Nov. 20, 2002. All prior applications are herein incorporated by reference in their entirety.

The present invention concerns a blood testing apparatus, an instrument for its operation and a method for operating the apparatus.

When making blood tests in the field, it is a desire to perform such tests with simple but reliable apparatus that can be handled even by relatively untrained personnel. Still, there exists the requirement that a blood sample shall be taken and handled under strict hygienic conditions, and that neither the sample itself, nor residues thereof, nor diluting or flushing liquids used when testing the sample shall risk to be contacted by humans. Thus, there shall be no waste matter and all contaminated material shall remain within the apparatus.

It is known in the state of art to count blood cells by causing a volume of diluted blood sample to pass a so-called capillary, i.e., an extremely small hole, generally in a ruby, the hole having a diameter considerably larger than the size of a blood cell, typically 80 μm. A voltage is applied over the capillary, and, when a blood cell passes through the hole, the electrical resistance changes. This is because the cells can be regarded as insulators. Each change in resistance can be detected by suitable electronic equipment, and the sum of all changes detected corresponds to the number of blood cells having passed through the capillary. In order to obtain the concentration of cells in the original sample, the concentration of cells in the diluted sample is multiplied by the dilution factor, typically 1:40000 when counting of red blood cells (RBC) is concerned. It is obvious, that measuring of sample volumes and dilution liquid volumes must be performed in an accurate and repeatable way such that not only a correct degree of dilution can always be guaranteed but also a thorough and uniform mixing of the two volumes is ensured.

A disposable sampling device for an apparatus for counting particles contained in a liquid, such as blood cells in a blood sample, is known from WO 99/01742. This device is capable of making one diluting step.

A blood testing apparatus for performing dilution of a small defined volume of blood sample contained in a capillary tube is described in U.S. Pat. No. 6,284,548. The dilution involves a pre-dilution step and a final dilution step.

A device for diluting and mixing a liquid sample, such as a blood sample for performing a CRP test, is described in WO 01/75416. The sample is contained in a capillary tube and is mixed in a first step with a diluting agent to provide a diluted sample. In a second step, a third medium, such as antibodies, may be mixed with the diluted sample.

Even if some of the prior art devices are capable of making two dilutions, none of them is capable of making two simultaneous dilutions to different dilution ratios, which is desirable in order to perform, e.g., simultaneous counting of white and red blood cells.

A disposable apparatus for use in blood testing, having one of the present co-inventors as single inventor, is described in SE 0103877-7 filed 21 Nov. 2001 and unpublished at the date of filing the present application. It presents one solution to the problem of providing such apparatus allowing simultaneous dilution of a blood sample to two defined dilutions ratios. It is also capable of retaining all contaminated material within itself.

This prior apparatus comprises a block-shaped housing having a first and a second receptacle; a first and a second cylinder, each having a piston moveable therein and each containing a defined volume of a diluent; a valve including a valve body having three valve body channels extending therethrough and being positionable in three distinct positions. In one position the receptacles are put in simultaneous communication with one each of the cylinders through pairs of the channels.

One of the receptacles, as a first means for receiving a blood sample, is adapted to receive a blood sampling capillary tube.

Although fulfilling the objectives stated, this apparatus presents some inconveniences. One relates to the manufacture of the block-shaped housing, which is expensive and complicated due to its various cylinders, and makes it unsuited for injection moulding. Another relates to the use of cylinders as means for containing the diluent, and pistons movable within the cylinders to displace the diluent. It manifests itself particularly during air transportation when the pistons tend to move uncontrolled due to a varying surrounding air pressure.

The present invention has as its object to present an alternative solution to problem of providing a disposable apparatus for use in blood testing allowing simultaneous dilution of a blood sample to two defined dilutions ratios and being capable of retaining all contaminated material within itself.

To fulfill this object, the present invention proposes the disposable apparatus having the characterizing features, an instrument for controlling the apparatus and a method of controlling the apparatus, as defined in the appended claims.

According to the present invention there is provided a block-shaped housing or cartridge having depressions in at least one of its sides. The depressions form and define main portions of receptacles and channels in the housing open towards the side of the housing in which they are formed. A diaphragm is positioned over at least portions of that side to seal the respective receptacles and channels and to define one Side thereof. Portions of the diaphragm positioned over receptacles are moveable relative to the plane of the side of the housing so as to cause a variation in the pressure within the receptacle, or, in response to a pressure variation, or, a volume variation therein. The channels interconnect the various receptacles and a valve provided within the housing to control flow between the receptacles.

An embodiment of the invention will now be described, reference being made to the accompanying drawings, wherein:

FIG. 2a is a perspective view of the capillary holder;

FIG. 11 is a schematic view showing the measuring step and the subsequent cleaning step.

Figure 1:
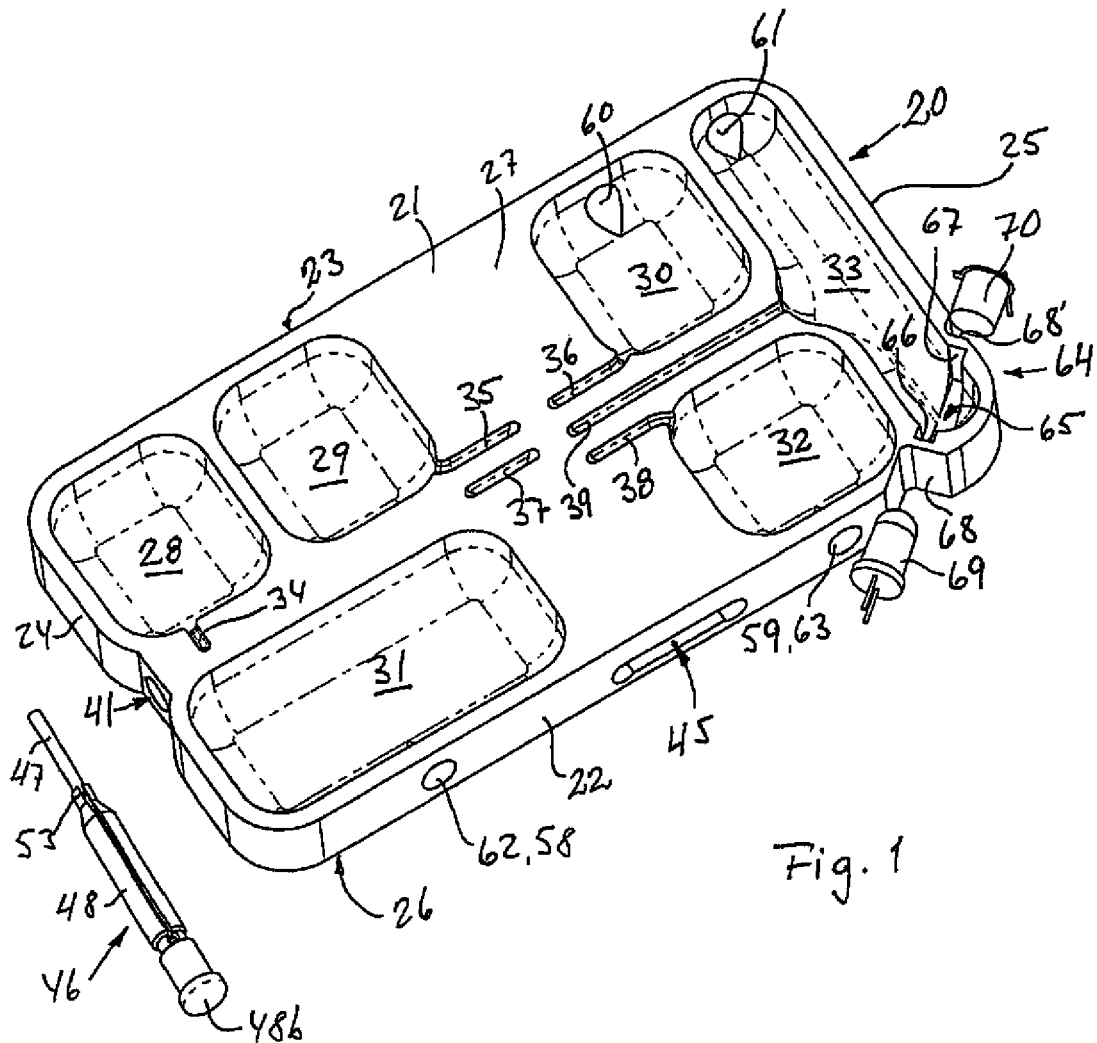
FIG. 1 is a perspective view of a cartridge having receptacles and channels in one of its sides, an associated sampling tube, and a photometer arrangement.

A cartridge 20 according to the present invention is shown in perspective in FIG. 1. It comprises a block-shaped, preferably molded housing 21 made from a preferably translucent material. It has a generally paralellepipedic shape including opposed longer side walls 22, 23, opposed shorter side walls 24, 25, a bottom side 26 and a top side 27. In the generally flat top side 27 is formed a plurality of depressions, in this embodiment six relatively large depressions defining receptacles 28-33, and five relatively narrow depressions defining channels 34-39.

A diaphragm 40 (FIGS. 2, 7, 8 and 10) is sealingly attached to the top side 27 of the housing 21 so as to cover all depressions forming the receptacles and channels and to seal them relative to the environment.

Figure 2:
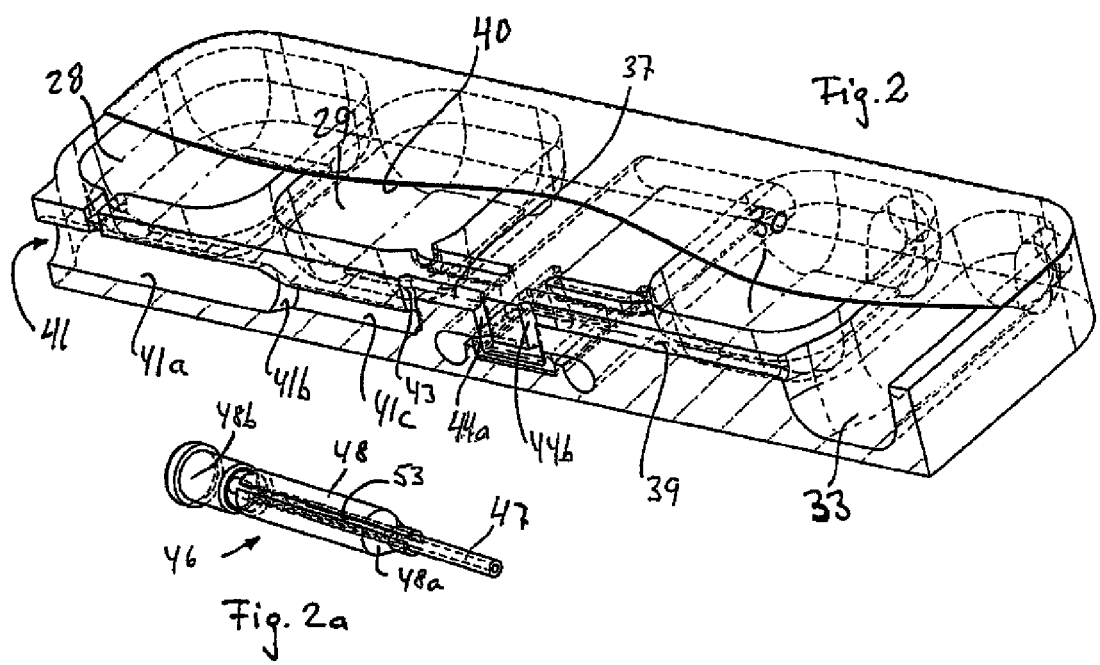
FIG. 2 is a perspective longitudinal central section through the cartridge of FIG. 1.
Figure 7:
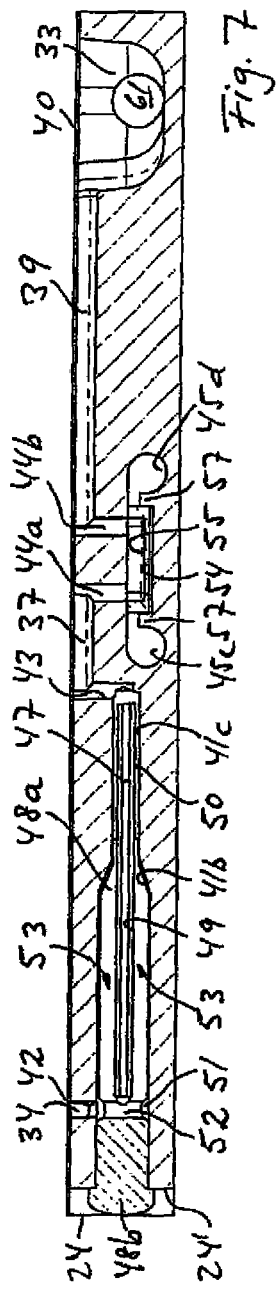
FIG. 7 is a longitudinal central section through the cartridge taken along line VII-VII in FIG. 8.
Figure 8:
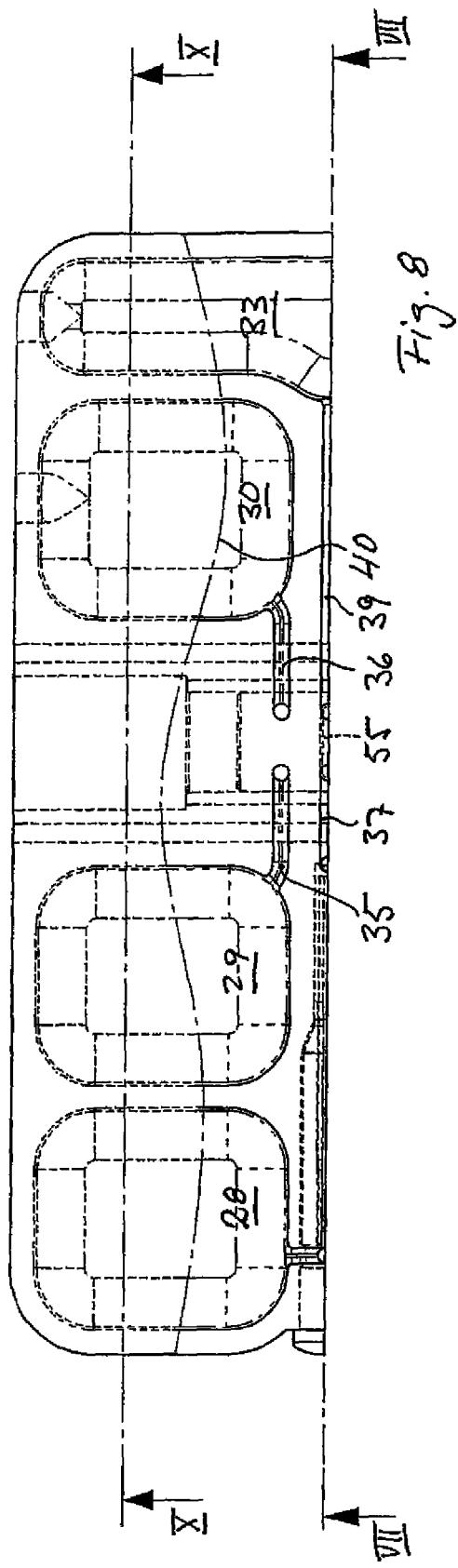
FIG. 8 is a plan view of one half of the cartridge showing portions of the diaphragm cut away.

A hole 41 extends centrally from the shorter side wall 24 towards the middle of the housing (see particularly FIGS. 2 and 7). It includes an outer, relatively wide, cylindrical portion 41a merging by an intermediate, frustoconical portion 41b with an inner, relatively narrow cylindrical portion 41c.

Relatively close to its exterior end, a hole 42 connects the hole portion 41a to one end of the channel 34, whose opposite end opens in the receptacle 28.

At the inner end of the hole 41, a hole 43 connects its more narrow portion 41c to a first end of the channel 37, whose second, opposite end connects to a hole 44a opening into an aperture 45 extending crosswise through the housing 21 between its longer side walls 21 and 22.

The opening 41 serves for receiving a holder 46 for a capillary tube 47 in the housing 21. The capillary holder is particularly shown in FIGS. 1 and 2a, and is shown sectioned in its entirely introduced state in FIG. 7. It comprises a body 48 fitting into the wider portion 41a of the hole 41 and having a frustoconical portion 48a matching the frustoconical portion 41b of the hole 41. A cap portion 48b in the rear end of the body 48 abuts a recessed portion 24' of the side wall 24 around the mouth of the hole 41 so as to limit the extent of introduction of the capillary holder into the hole 41 (FIG. 7). A central hole 49 extending from the forward end of the capillary holder 46 receives a major portion of the capillary tube 47, the forward, free end of which opens close to where the hole 43 opens into the narrow portion 41c of the hole 41. The capillary tube 47 has a smaller outer diameter than the inner diameter of the hole portion 41c, thus leaving an annular space 50 between the capillary tube and the wall of the hole portion 41c. An annular groove 51 is formed in the body 48 to be located opposite to the hole 42, and a cross-hole 52 extends diametrically therethrough to open at opposed locations in the groove 51. The hole 52 intersects the hole 49 so as to establish communication between the annular groove 51 and the capillary tube 47 via the cross-hole 52, and, thereby, from the receptacle 28, through the channel 34, the hole 42, the groove 51, the cross-hole 52, the capillary tube 47, and the hole 43 to the channel 37.

As partly seen in FIG. 1 and more clearly in FIG. 7, the body 48 of the capillary holder 46 has a slot 53 extending from its foremost end to the annular groove 51, thus establishing communication between the annular space 50 and the annular groove 51. The slot 53 also makes the capillary holder flexible so as to facilitate introduction of the capillary tube 47 therein.

In the aperture 45 open one respective end of the channels 35, 36, 37, 38 and 39. The respective opposite end of these channels open in the receptacles 29, 30, 32 and 33.

Channels 35 and 36 are aligned, as are channels 37 and 39.

Channels 35 and 37 are mutually parallel, as are channels 36, 38 and 39. The lateral spacing between channels 35 and 37 is equal to that between channels 36 and 39 as well as between channels 39 and 38.

Figure 9:
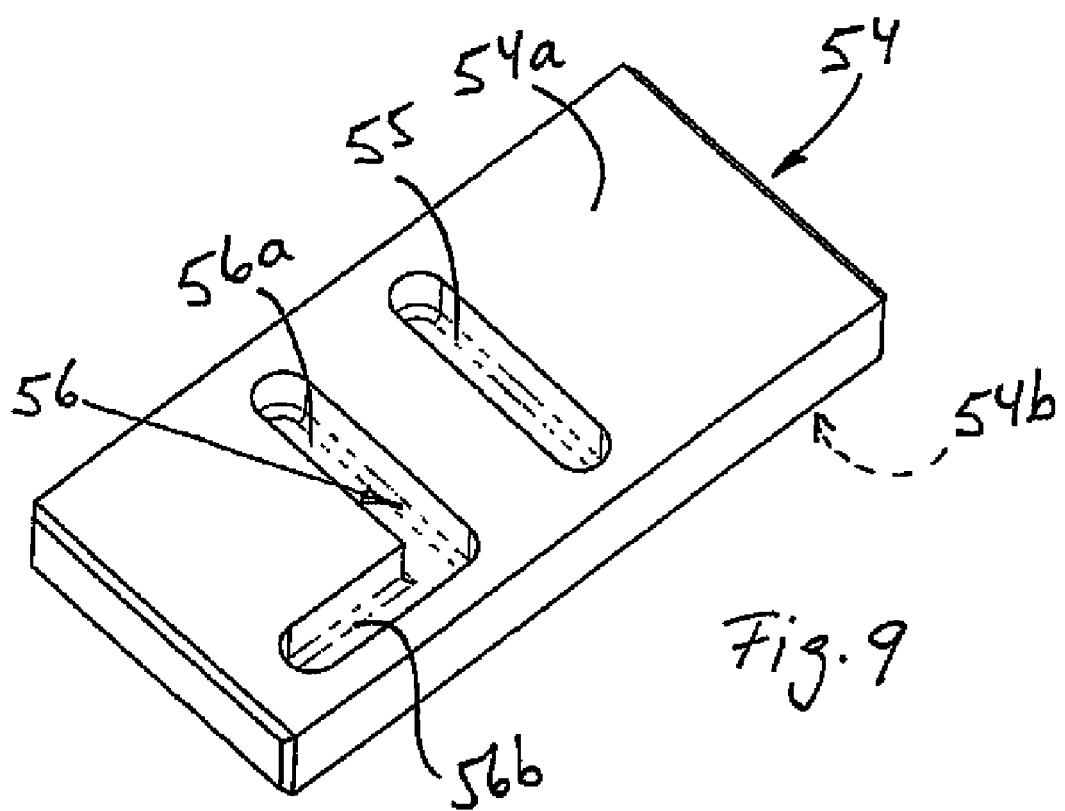
FIG. 9 is a perspective view of the valve slide.

The aperture 45 serves to slidingly receive a valve slide 54 shown in FIGS. 2 and 7, and separately shown in FIG. 9. It comprises a parallelepipedic body having opposed parallel surfaces 54a, 54b. In the surface 54a is formed a straight channel 55 extending in the crosswise direction of the aperture 45 and having a well-defined volume, typically 10 μl, and an L-shaped channel 56 having a first leg 56a extending in the crosswise direction of the aperture 45, i.e., parallel to the straight channel 55, and a second leg 56b extending perpendicularly thereto. The spacing between the channel 55 and the first leg 56a is equal to the lateral spacing between the channels 35/37 and 36/39/38, and the length of the second leg 56b is equal to the spacing between the channels 36 and 38.

Figure 10:
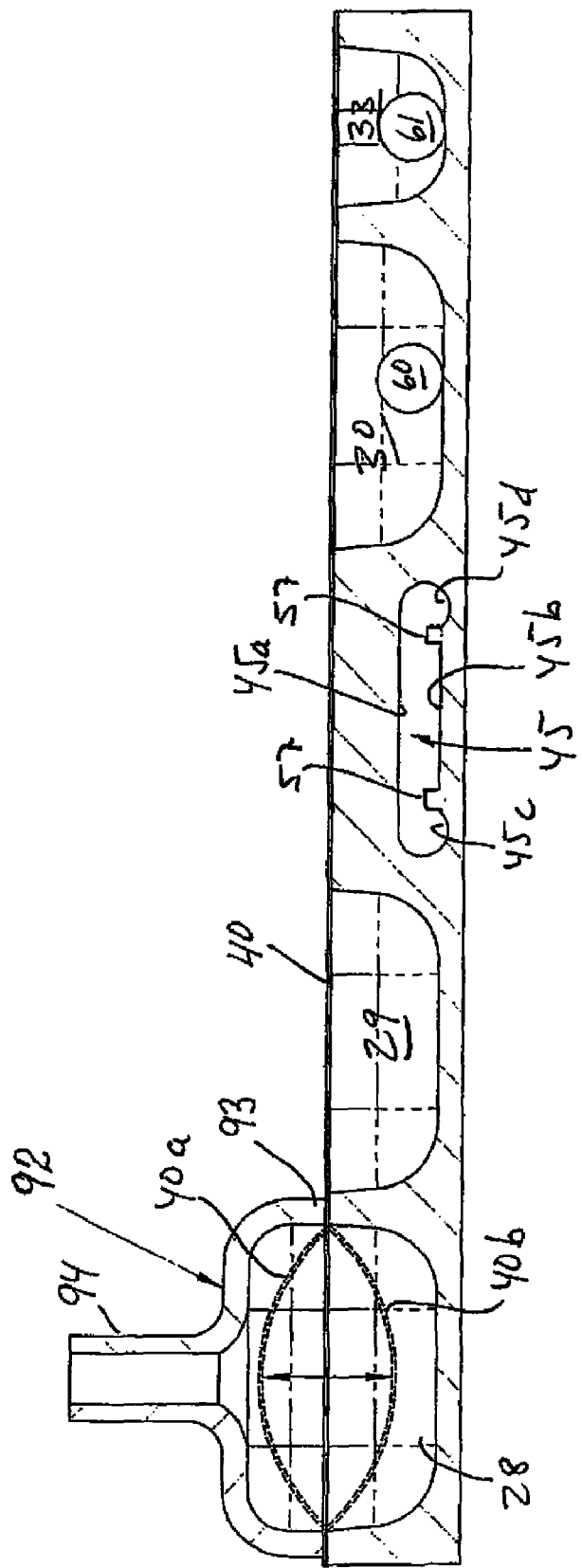
FIG. 10 is a section through the cartridge taken along line X-X in FIG. 8 showing more in detail the operation of the device.

The cross-sectional shape of the aperture 45 appears best from FIG. 10. It includes a central portion having parallel sides 45a, 45b for slidingly supporting the valve slide surfaces 54a, 54b, respectively. The valve slide 54 is laterally guided by parallel ribs 57 protruding from the surface 45b. In order not to make the material between the side 45b of the aperture and the bottom surface 26 of the body 21 flex due to introduction of the valve slide into the aperture 45, the aperture is widened beyond the ribs 57, and the material thickness is reduced along parallel, part-cylindrical recesses 45c, 45d, thereby imparting the remaining material spring properties urging the valve slide 54 towards the surface 45a of the aperture 45. Alternatively, the slide may be made with a certain degree of resilience to ensure proper sealing.

In the opposed longer side walls 22 and 23 of the housing are provided openings 58, 59, 60 and 61 providing access to the receptacles 31, 32, 30 and 33, respectively. After filling of these receptacles (see below), the openings are closed by plugs that are pierceable by an injection needle or the like in order to inject a fluid into or retract a fluid from the respective receptacles of the plugs, only plugs 62 and 63 sealing receptacles 31 and 32, respectively, are seen in FIG. 1.

The sequence of operation of the cartridge 20 will now be described with reference to FIGS. 3-6 showing four subsequent steps.

Figure 3:
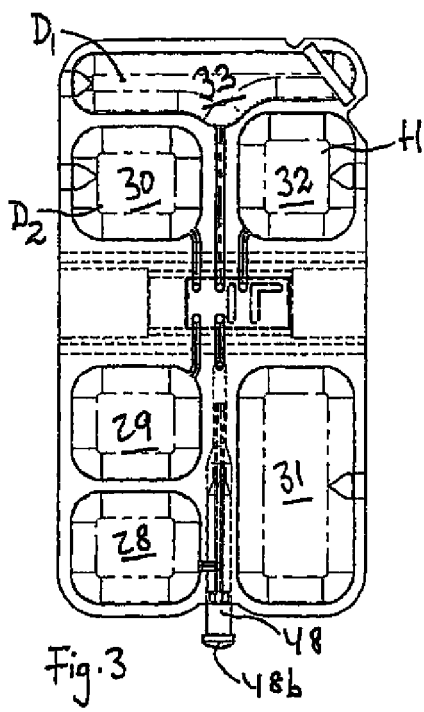
FIG. 3 is a plan view showing the cartridge in its transport position.

In FIG. 3 is shown the preparatory or transport position of the cartridge 20. In advance, a well-defined volume, typically 2 ml, of a liquid diluting agent $D_1$ has been filled into the receptacle 33 having a capacity of typically 3 ml. Likewise, a well-defined volume, typically 2 ml, of a liquid diluting agent $D_2$ has been filled into the receptacle 30 also having a capacity of typically 3 ml. The diluting agents are typically an isotonic sodium chloride solution. Furthermore, a well-defined volume, typically 2 ml of a liquid hemolysis agent H has been filled into the receptacle 32, typically having a capacity of 2 ml. (It should be noted here, that a dry hemolysis agent may be used as an alternative.) Finally, the receptacle 31, typically having a capacity of 3 ml, is filled with a washing liquid, typically isotonic sodium chloride solution. The receptacles 29 and 28, each typically having a capacity of 1 ml, are empty.

In the transport position, the capillary holder 46 is not completely introduced into the hole 41. The valve slide 54 is in a position where the mouths of the channels 35, 36, 37, 38 and 39 are covered by smooth, unrecessed portions of the valve slide surface 54a. Consequently, all these channels are closed in relation to the valve slide.

Figure 4:
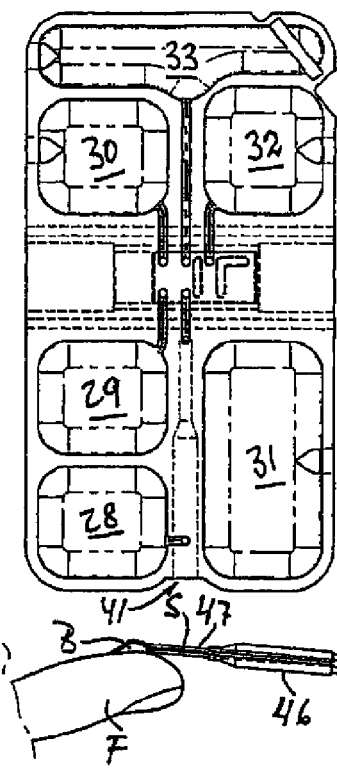
FIG. 4 is a plan view showing the cartridge in its sampling position and also showing the sampling device and a portion of a finger tip.

FIG. 4 shows the sampling position. The capillary holder has been pulled out of the hole 41, and a blood sample S is taken with the capillary tube as illustrated in FIG. 4. The tube is approached to a drop of blood B formed on a punctured finger tip F, and the drop is sucked up by capillary action to completely fill the capillary tube 46 with a defined volume of sample S, typically 10 μl. After the sample is taken, the capillary tube is re-inserted into the hole 41 and pushed into its fully inserted position shown in FIG. 7. In that position, the rear portion of the capillary holder body 48 having a non-shown O-ring effectively seals the body 48 in the hole 41. The valve slide is still in its original position.

Figure 5:
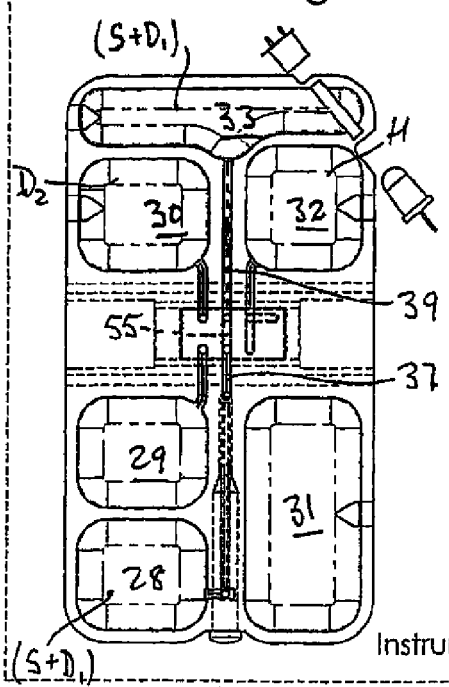
FIG. 5 is a plan view showing the cartridge in its first dilution or mixing position.

FIG. 5 shows the first diluting or mixing step. The valve slide 54 is displaced such that one end of its cross-channel 55 communicates with the channel 37 and the other end thereof communicates with the channel 39. Since the annular groove 52 is located opposite to the hole 42 in the fully introduced position, communication is now established between the receptacle 28 and the receptacle 33.

Now, diluting agent $D_1$ is caused to flow from the receptacle 33 through the channel 39, the valve channel 55, and the channel 37 into the relatively narrow portion 41c of the hole 41. There, a part of the flow is directed through the capillary tube 47, thus displacing the blood sample S contained therein into the cross-channel 52 and the annular groove 51. Another part of the flow is directed along the exterior of the protruding end of the capillary tube into the slot 53 and from there into the cross-channel 52 and the annular groove 51 where it meets the blood sample and mixes therewith and dilutes it. Together the two flows will end up in the receptacle 28. The mixture is then caused to flow back along the same two paths into the receptacle 33, where it mixes with the remainder of the diluting agent $D_1$ still contained therein.

The flow back and forth is repeated until a proper mixing is ensured. When the first mixing step is completed, a defined volume of first step diluted sample $(S+D_1)$ remains within the valve slide channel 55. This is due to the typical volume relations between the receptacles 28 and 33, that ensures that the receptacle 33 will never be emptied. With the typical volumes stated, the dilution ratio after the first step is 1:200.

Figure 6:
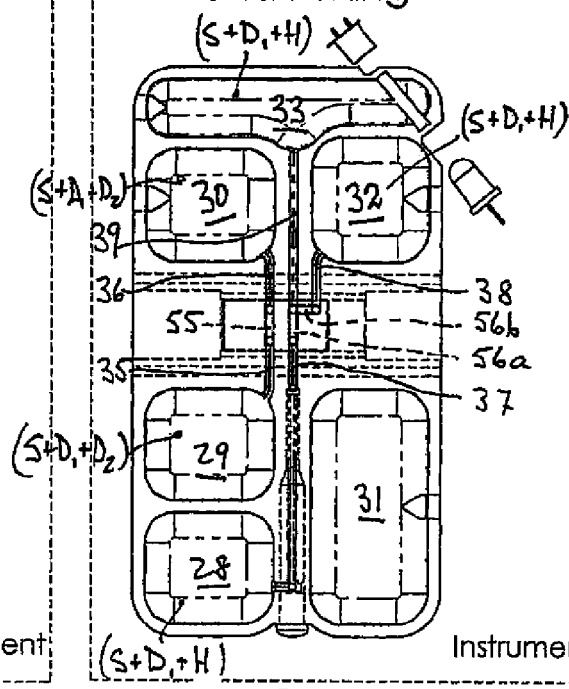
FIG. 6 is a plan view showing the cartridge in its second dilution or mixing position.

The second dilution and mixing step is shown in FIG. 6. The valve slide 54 is further displaced such that one end of its cross-channel 55 communicates with the channel 35 and the other end thereof communicates with the channel 36, thus establishing communication between the receptacles 29 and 30.

In the displacement of the valve slide, the defined volume of first stage diluted sample previously entrapped in the slide channel 55 is brought along. Simultaneously, one end of the first leg 56a of the L-shaped channel 56 is brought into communication with the channel 37, one end of the second leg 56b is brought into communication with the channel 38, and the common other end of the legs 56a and 56b is brought into communication with the channel 39. Thus, there is established simultaneous communication between the receptacles 28, 32 and 33.

The second mixing step includes two parallel parts.

A first part takes place between receptacles 29 and 30. The diluting liquid $D_2$ in the receptacle 30 is caused to flow through the channel 36, into the slide channel 55 displacing the entrapped volume of first stage diluted sample, through the channel 35 and into the originally empty receptacle 29.

As before, the mixture is then caused to flow back and forth along the same path until a proper mixing is ensured. This first part of the second mixing step is stopped with the two step diluted sample $(S+D_1+D_2)$ remaining in the receptacle 30, resulting, with the typical volumes stated, in a dilution ratio of 1:40000. This dilution ratio is typical for RBC testing.

A second part takes place between the receptacles 28, 32 and 33, the receptacles 28 and 33 both containing the first step diluted sample $(S+D_1)$ and the receptacle 32 containing a hemolysis agent H. The liquids are caused to flow back and forth between the three receptacles until a proper mixing is ensured. In case the hemolysis agent is dry, it will be successively dissolved during the repeated flushing of the receptacle 32. The second part of the second mixing step is stopped with a main portion of the mixture $(S+D_1+H)$ remaining within the receptacle 33. This mixture has a dilution ratio of 1:400 with the typical volumes stated, and is for white blood cell testing.

The housing 21 is preferably made from a translucent synthetic resin. This enables the provision of a light path 64 through the housing. A portion of the receptacle 33 is formed with a recess 65 having an accurately defined length and parallel end walls 66, 67. The recess extends diagonally across a corner of the housing 21, and the walls 22 and 25 of the housing are formed with planar wall portions 68, 68', parallel to the respective end wall 66, 67. The light path further includes a light source 69, preferably a light diode, and a light sensor 70. The light path enables photometric determination of certain parameters of the liquid contained in the receptacle 33, such as, initially, a reference value of the diluting liquid and the opposed walls of the recess 65, and then certain values of the final mixture.

Other tests to be performed on the diluted samples contained within the receptacles 30 and 33, involve withdrawal of fluid from the respective receptacles. This is performed by a measurement system schematically shown in FIG. 11. It includes two conduits 71, 72, each starting with a needle portion 73, 74, respectively. The needle portions are inserted through the respective plug sealing the openings 60, 61 into the receptacles 30, 33, respectively. Each of the conduits 71, 72 is provided with a cell counting station, each comprising an orifice 75, 76. As is known in the art, the orifices are small apertures allowing statistically only one blood cell to pass at a time. By means of non-shown electric wires, a voltage may be applied over the orifices, and any change in the resistance across the orifices, indicating the passage of a blood cell to be counted, may be detected by suitable electronic equipment included in the system, and the sum of all resistance changes detected corresponds to the number of blood cells having passed through the orifice.

Each of the conduits 71, 72 has a branch 77, 78, including a valve 79, 80, and a measuring portion 81, 82, respectively.

The measuring portions are provided with counting start detectors 81a, 82a and counting stop detectors 81b, 82b spaced defined distances.

The branches 77, 78 are joined to a common conduit 83 having a valve 84 and a pump 85 therein. A branch 86 from the conduit 83 between the branches 77, 78 and the valve 84 has a valve 87 and is open to the atmosphere.

Beyond the respective branch 77, 78, the conduits 71, 72 have a valve 88, 89, respectively, and are joined to a common conduit 90 having in its end a needle portion 91 introduced through the non-shown plug 62 into the receptacle 31 containing washing liquid.

In the start position of measurement, the conduits 71, 72, and possibly also the conduit 90, are filled with a liquid, typically the same isotonic sodium chloride solution as that used in receptacles 30 and 31. The valves 88, 89 and 87 are closed, whereas the valves 79, 80 and 84 are opened. The pump 85 is started to withdraw liquid from the receptacles 30 and 33. When the liquid originally in the conduits 71 and 72 reach the respective counting start detector 81*a*, 82*a*, counting in the orifices 75, 76 is started. At that time, liquid from the respective receptacle 30, 33 has reached the orifices.

Counting stops when the liquid has reached the respective counting stop detector 81*b*, 82*b*. At that time, liquid from the receptacles 30, 33 may not have reached into the branches 77, 78.

Subsequently, the valve 84 is closed and the valve 87 is opened, whereupon liquid is caused to return to the receptacles 30, 33, thereby returning the liquid within the measuring portions 81, 82 at least to the counting start detectors 81*a*, 82*a*. Then the valves 79, 80 and 87 are closed, and the valves 88 and 89 are opened to perform a cleaning step.

In the cleaning step, more liquid is caused to enter the receptacles 30 and 33, but is now withdrawn from the receptacle 31 at least until fresh liquid therefrom has reached both receptacles 30, 33. In this position, with all possibly contaminated objects and liquids safely kept within the cartridge, the needles 73, 74, 91 are withdrawn, and the cartridge is disposed of.

To perform displacement of liquids from and to the various receptacles, there are various methods available, from simply pressing a finger against a portion of the diaphragm 40 over a chosen receptacle, to applying a hydraulic or pneumatic pressure over selected portions of the diaphragm. According to the present invention it is preferred to apply a vacuum over portions of the diaphragm corresponding to a selected receptacle. To perform this operation, the cartridge is placed in an instrument indicated in FIGS. 5 and 6, including also the measurement system shown in FIG. 11. In FIG. 10, merely a portion of the instrument is shown. It includes a plurality of vacuum domes having outlines corresponding to those of selected receptacles. A vacuum dome 92, as a pressure actuating component, is shown to be located over the receptacle 28. It has a rim 93 sealing against the diaphragm 40 and a tubular stem portion 94 attachable to a non-shown source of vacuum. A vacuum applied in the dome 92 causes the diaphragm 40 to strive to adopt the upwardly convex shape illustrated at 40*a*, thus sucking liquid into the receptacle 28 from, e.g., the receptacle 33 in the position according to FIG. 5. A vacuum applied to the corresponding vacuum dome associated with the receptacle 33 causes the liquid to be withdrawn from the receptacle 28 and the diaphragm to assume the shape indicated at 40*b*. Evidently, the same shape would result from an overpressure within the vacuum dome.

Although a slide valve has been described herein, it is obvious that other kinds of valves may be used, such as primarily a turning valve.

Also, it is within the scope of the present invention to provide an apparatus having depressions defining receptacles and channels in more than one of its sides, e.g., in two opposite sides, and a valve between these sides.

What is claimed is:

1. A blood test instrument comprising:
   (a) a cell counting station comprising an orifice permitting blood cells in a fluid passing therethrough one at a time, and equipped to enumerate said blood cells when said blood cells pass through said orifice;
   (b) a pressure actuating component adapted to apply a pressure alternately on two flexible receptacles of a disposable cartridge removably placed within said instrument to cause flowing of a mixture of a blood sample and a liquid agent back and forth between said two receptacles to affect mixing of said mixture within said cartridge; and
   (c) a first conduit connecting to said cell counting station at one end and having a piercing component at another end, said piercing component disposed adjacent to said disposable cartridge and adapted to be inserted to one of said receptacles to deliver said mixture contained in said cartridge to pass through said orifice of said cell counting station for counting.

2. The blood test instrument of claim 1, wherein said pressure actuating component is means enabling applying a hydraulic or pneumatic pressure, or means enabling applying vacuum or pressure on said flexible receptacles of said disposable cartridge in an alternate manner.

3. The blood test instrument of claim 2, wherein said pressure actuating component is vacuum means comprising a plurality of vacuum domes.

4. The blood test instrument of claim 1 further comprising a pump connected to said cell counting station, adapted to withdraw said mixture from said receptacles through said first conduit to said orifice of said cell counting station for counting.

5. The blood test instrument of claim 4 further comprising a second conduit connecting, at one end, to said first conduit and said pump through one or more valves, and having a piercing component at another end, adapted to be inserted into a further receptacle of said cartridge containing a washing liquid.

6. The blood test instrument of claim 5, wherein when said piercing component of said first conduit is inserted into said one of said receptacles containing said mixture and said piercing component of said second conduit is inserted into said further receptacle containing said wash liquid, said instrument enables withdrawing said washing liquid from said cartridge through said second conduit into said first conduit, thereby cleaning said instrument and causing returning of said mixture inside said instrument back into said receptacles of said cartridge after counting said mixture in said cell counting station.

7. The blood test instrument of claim 5 further comprising a further cell counting station comprising a second orifice permitting blood cells in a further fluid passing therethrough one at a time, and equipped to enumerate said blood cells when said blood cells pass through said second orifice; and a third conduit connecting to said further cell counting station at one end and having a piercing component at another end, adapted to be inserted to another of said receptacles of said cartridge for delivering a content therein to said further cell counting station; wherein said pressure actuating component is further adapted to apply a pressure alternately on said another receptacle and an interconnected receptacle of said disposable cartridge to cause flowing of a mixture of said blood sample and a further liquid agent therebetween.

8. The blood test instrument of claim 7, wherein said second conduit further connects to said third conduit through one or more valves.

9. The blood test instrument of claim 8, wherein when said piercing components of said first conduit and said third conduit are inserted into respective receptacles of said cartridge and said piercing component of said second conduit is inserted into said further receptacle containing said wash liquid, said instrument enables withdrawing said washing liquid from said cartridge through said second conduit into said first and third conduits, thereby cleaning said instrument and causing returning of said mixtures inside said instrument back into said respective receptacles of said cartridge after counting said mixtures in said cell counting stations.

10. The blood test instrument of claim 7, wherein each of said cell counting stations is an electrical resistance measurement device.

11. The blood test instrument of claim 10, wherein one of said cell counting stations is equipped for counting red blood cells, and one of said cell counting stations is equipped for white blood cells of said blood sample, respectively.

12. A method of measuring a blood sample on a blood test instrument using a disposable cartridge comprising:
   (a) providing a disposable cartridge comprising multiple receptacles formed between multiple depressions of a housing and a diaphragm sealing said depressions, and multiple channels adapted to connect said receptacles; portions of said diaphragm above said multiple depressions being flexible; at least one of said multiple receptacles containing a liquid agent;
   (b) introducing a blood sample into said cartridge;
   (c) placing said cartridge into a blood test instrument, said instrument comprising a cell counting station comprising an orifice permitting blood cells in a fluid passing therethrough one at a time, and equipped to enumerate said blood cells when said blood cells pass through said orifice; a pressure actuating component adapted to apply a pressure alternately on said flexible portions of two of said receptacles of said disposable cartridge; and a first conduit connecting to said cell counting station at one end and having a piercing component at another end, said piercing component disposed adjacent to said disposable cartridge and adapted to be inserted to one of said receptacles of said cartridge;
   (d) applying a pressure on said receptacle containing said liquid agent to cause displacement of said liquid agent into another receptacle through one of said channels containing said blood sample;
   (e) applying a pressure alternately on said receptacle containing said liquid agent and said another receptacle to cause flowing of a mixture of said blood sample and said liquid agent back and forth between said receptacles to obtain proper mixing of said mixture within said cartridge;
   (f) thereafter, inserting said piercing component into said receptacle containing said liquid agent or said another receptacle and delivering said mixture through said first conduit to said cell counting station; and
   (g) counting blood cells in said mixture as said blood cells pass through said orifice of said cell counting station one at a time.

13. The method of claim 12 further comprising returning said mixture to said receptacles of said cartridge through said first conduit after said counting.

14. The method of claim 13 further comprising inserting a piercing component of a second conduit of said instrument into one of said receptacles of said cartridge containing a washing liquid and withdrawing said wash liquid through said second conduit into said first conduit to clean said instrument and to cause all of said mixture returning to said cartridge.

15. The method of claim 14 further comprising withdrawing said piercing components of said first and second conduits from said cartridge and disposing said cartridge.

* * * * *